(12) United States Patent
Okerlund et al.

(10) Patent No.: US 7,343,196 B2
(45) Date of Patent: Mar. 11, 2008

(54) CARDIAC CT SYSTEM AND METHOD FOR PLANNING AND TREATMENT OF BIVENTRICULAR PACING USING EPICARDIAL LEAD

(75) Inventors: Darin R. Okerlund, Muskego, WI (US); Jasbir S. Sra, W305 N2963 Red Oak Ct., Pewaukee, WI (US) 53072; Shankara B. Reddy, Cedarburg, WI (US); Laurent Launay, St. Remy Pes Chevreube (FR); Melissa L. Vass, Milwaukee, WI (US)

(73) Assignees: GE Medical Systems Global Technology Company LLC, Waukesha, WI (US); Jasbir S. Sra, Peewaukee, WI (US)

( * ) Notice: Subject to any disclaimer, the term of this patent is extended or adjusted under 35 U.S.C. 154(b) by 454 days.

(21) Appl. No.: 10/249,815

(22) Filed: May 9, 2003

(65) Prior Publication Data

US 2004/0225328 A1   Nov. 11, 2004

(51) Int. Cl.
*A61B 5/05* (2006.01)
(52) U.S. Cl. .............. 600/424; 606/130; 600/429
(58) Field of Classification Search .......... 600/424, 600/427, 374; 606/130
See application file for complete search history.

(56) References Cited

U.S. PATENT DOCUMENTS

| | | | |
|---|---|---|---|
| 3,954,098 A | 5/1976 | Dick et al. ............. | 128/2.05 |
| 4,364,397 A | 12/1982 | Citron et al. | |
| 4,574,807 A | 3/1986 | Hewson et al. ....... | 128/419 PG |
| 5,245,287 A | 9/1993 | Nowak et al. .......... | 324/322 |
| 5,274,551 A | 12/1993 | Corby, Jr. .............. | 364/413.13 |
| 5,304,212 A | 4/1994 | Czeisler et al. .......... | 607/88 |
| 5,348,020 A | 9/1994 | Huston ................ | 128/696 |
| 5,353,795 A | 10/1994 | Souza et al. ............ | 128/653.2 |
| 5,391,199 A | 2/1995 | Ben-Haim ............. | 607/122 |
| 5,431,688 A | 7/1995 | Freeman ............... | 607/10 |
| 5,515,849 A | 5/1996 | Murashita et al. | |
| 5,568,384 A | 10/1996 | Robb et al. ............ | 364/419.13 |
| 5,738,096 A | 4/1998 | Ben-Haim ............. | 128/653.1 |

(Continued)

FOREIGN PATENT DOCUMENTS

EP    1182619 A2    2/2002

(Continued)

OTHER PUBLICATIONS

PCT Search Report for PCT/US2004/020909.

(Continued)

*Primary Examiner*—Brian L. Casler
*Assistant Examiner*—John F. Ramirez
(74) *Attorney, Agent, or Firm*—Cantor Colburn LLP

(57) ABSTRACT

A method for planning biventricular pacing lead placement for a patient includes obtaining acquisition data from a medical imaging system and generating a 3D model of the left ventricle and thoracic wall of the patient. One or more left ventricle anatomical landmarks are identified on the 3D model, and saved views of the 3D model are registered on an interventional system. One or more of the registered saved views are visualized with the interventional system, and at least one suitable region on the left ventricle wall is identified for epicardial lead placement.

37 Claims, 2 Drawing Sheets

U.S. PATENT DOCUMENTS

| | | | |
|---|---|---|---|
| 5,765,561 A | 6/1998 | Chen et al. | |
| 5,823,958 A | 10/1998 | Truppe | 600/426 |
| 5,839,440 A | 11/1998 | Liou et al. | 128/654 |
| 5,951,475 A | 9/1999 | Gueziec et al. | 600/425 |
| 6,058,218 A | 5/2000 | Cline | |
| 6,081,577 A | 6/2000 | Webber | 378/23 |
| 6,208,347 B1 | 3/2001 | Migdal | 345/419 |
| 6,235,038 B1 | 5/2001 | Hunter et al. | 606/130 |
| 6,246,898 B1* | 6/2001 | Vesely et al. | 600/424 |
| 6,266,553 B1 | 7/2001 | Fluhrer et al. | 600/428 |
| 6,289,115 B1 | 9/2001 | Takeo | 382/130 |
| 6,289,239 B1 | 9/2001 | Panescu et al. | 600/523 |
| 6,314,310 B1 | 11/2001 | Ben-Haim et al. | 600/424 |
| 6,389,104 B1 | 5/2002 | Bani-Hashemi et al. | 378/98.12 |
| 6,456,867 B2 | 9/2002 | Reisfeld | 600/407 |
| 6,468,265 B1 | 10/2002 | Evans et al. | 606/1 |
| 6,490,475 B1 | 12/2002 | Seeley et al. | 600/426 |
| 6,490,479 B2 | 12/2002 | Bock | 600/518 |
| 6,504,894 B2 | 1/2003 | Pan | 378/8 |
| 6,549,606 B1 | 4/2003 | Vaillant et al. | 378/4 |
| 6,556,695 B1 | 4/2003 | Packer et al. | 382/128 |
| 6,584,343 B1 | 6/2003 | Ransbury et al. | 600/509 |
| 6,650,927 B1 | 11/2003 | Keidar | 600/424 |
| 6,782,284 B1 | 8/2004 | Subramanyan et al. | 600/407 |
| 6,950,689 B1 | 9/2005 | Willis et al. | |
| 7,047,060 B1 | 5/2006 | Wu | |
| 2002/0042570 A1 | 4/2002 | Schaldach et al. | |
| 2003/0018251 A1 | 1/2003 | Solomon | 600/427 |
| 2003/0097219 A1 | 5/2003 | O'Donnell et al. | 702/19 |
| 2003/0120264 A1 | 6/2003 | Lattouf | |
| 2003/0187358 A1 | 10/2003 | Okerlund et al. | 600/443 |
| 2003/0220557 A1 | 11/2003 | Cleary et al. | 600/409 |
| 2004/0027347 A1 | 2/2004 | Farsaie | 345/419 |
| 2004/0087850 A1 | 5/2004 | Okerlund et al. | 600/407 |
| 2004/0225212 A1 | 11/2004 | Okerlund et al. | 600/407 |
| 2004/0225331 A1 | 11/2004 | Okerlund et al. | 607/14 |

FOREIGN PATENT DOCUMENTS

| | | |
|---|---|---|
| EP | 1321101 A2 | 12/2002 |
| WO | WO 91/07726 | 5/1991 |
| WO | WO 96/10949 | 4/1996 |

OTHER PUBLICATIONS

F. H.M. Wittkampf et al.; "Loca Lisa—New Technique for Real-Time 3-Dimensional Localization of Regular Intracardiac Electrodes," *Circulationh*; 1999; 99: 1312-1317.

H. Nikagawa et al., "Role of the Tricuspid Annulus and the Eustachian Valve/Ridge on Atrial Flutter: Relevance to Catheter Ablation of the Septal Isthmus and a New Technique for Rapid Identification of Ablation Success," *Circulation* 1996; 94:407-24.

L. Gepstein et al., "A Novel Method for Nonfluoroscopic Catheter-Based Electroanatomical Mapping of the Heart: In Vitro and In Vivo Accuracy Results;" *Circulation* 1997; 95:1611-22.

S. Shpun et al., "Guidance of Radiofrequency Endocardial Ablation with Real-time Three-dimensional Magnetic Navigation System;" *Circulation* 1997; 96:2016-21.

J. Sra et al., "Electroanatomic Mapping to Identify Breakthrough Sites in Recurrent Typical Human Flutter," *Paceing Clin. Electrophysiol* 2000; 23; 1479-92.

R.J. Schilling et al.; "Simultaneous Endocardial Mapping in the Human Left Ventricle Using a Noncontact Catheter: Comparison of Contact and Reconstructured Electrograms During Sinus Rhythm;" *Circulation* 1998; 98:997-98.

C. C. Gornick et al., "Validation of a New Noncontact Catheter System for Electroanatomic Mapping of Left Ventricular Endocardium;" *Circulation* 1999; 99:829-835.

J. Sra et al., "Noncontact Mapping for Radiofrequency Ablation of Complex Cardiac Arrhythmias;" *J. Interven. Cardiac Electrophysiol* 2001; 5:323-331.

N. M.S. de Groot et al., "Three-Dimensional Catheter Positioning During Radiofrequency Ablation in Patients: First Application of a Real-Time Position Management System;" *J. Interven. Cardiac Electrophysiol* 2001; Nov. 11(11):1183-92.

J. Schreieck et al., "Radiofrequency Ablation of Cardiac Arrhythmias Using a Three-Dimensional Real-Time Position Management and Mapping System;" *Pacing Clin. Ekectrophysiol.* Dec. 2002, 25(12):1699-707.

F. Wittkampf et al., "Real-Time, Three-Dimensional, Nonfluoroscopic Localization of the Lasso Catheter;" *J. Interven. Cardiac Electrophysioll* 2002, 13:630.

J. Sra et al., "Cardiac Chamber Geometry Construction, Catheter Navication and Ablation Using Cutaneous Patches;" *Supplement to Circulation* Oct. 2003, 108(17): IV-585, Abstract 2667.

J. Sra et al., "Three Dimensional Right Atrial Geometry Construction and Catheter Tracking Using Cutaneous Patches;" *J. Interven. Cardiac Electrophysiol*, 2003 14:897.

Z. Zhang; "Iterative Point Matching for Registration of Free-Form Curves;" *Inria* 1992, pp. 1-40.

C.L. Grines et al.; "Functional Abnormalities in Isolated Left Bundle Branch Block: The Effect of Interventricular Asynchrony;" *Circulation*; 1989; 79:845-53.

H. B. Xia et al., "Differing effects of right ventricular pacing and left bundle branch block on left ventricular function;" *Br. Heart J.*, 1993; 69:166-173.

S. Cazeau et al., "Effects of Multisite Biventricular Pacing in Patients with Heart Failure and Intraventricular Conduction Delay;" *N. Engl. J. Med.* 2001; 344:873-880.

M. V. Pitzalis et al., "Cardiac Resynchronization Therapy Tailored by Echocardiographic Evaluation of Ventricular Acnchrony," *J. Am. Coll. Cardiol.* 2002; 40:1615-22.

W. T. Abraham et al., "Cardiac Resynchronization in Chronic Heart Failure;" *N. Engl. J. Med.* 2002; 346:1845-1853.

C. A. Pelizzari et al., "Accurate Three-Dimensional Registration of CT, PET, and/or MR Images of the Brain;" *J. Comput. Assist. Tomogr.* 1989; 13:20-26.

A.C. Evans et al.; "MRI-PET Correlation in Three Dimensions Using a Volume-of-Interest (VOI) Atlas;" *J. Cerb Flow Metab.* 1991; 11:A69-A78.

R.P. Woods et al.; "Rapid Automated Algorithm for Aligning and Reslicing PET Images;" *Journal of Computer Assisted Tomography*, 1992; 16:620-633.

B.A. Ardekani et al.; "A Fully Automatic Multimodality Image Registration Algorithm;" *Journal of Computer Assisted Tomography*; 1995; 19:615-623.

L. Thurfell et al.; "Registration of Neuroimaging Data: Implementation and Clinical Applications;" *American Society of Neuroimaging*; 2000; 10:39-46.

S. A. Ben-Haim et al.; "Nonfluoroscopic, in vivo navigation and mapping technology;" *Nature Medicine*; 1996, 2:1393-5.

B. Taccardi et al.; " A new intracaitary probe for detecting the site of origin of ectopic ventricular beats during one cardiac cycle;" *Circulation*; 1987; 75:272-81.

F. H.M. Wittkampf et al.; "New Technique for Real-Time 3-Dimensional Localization of Regular Intracardiac Electrodes;" *Circulation*; 1999; 99:1312-17.

V. Fuster et al. "ACC/AHA/NASPE 2002 Guidelines Update for Implantation of Pacemakers and Antiarrhythmia Devices;" J. Am. Coll. Cardiol 2001; 38:1-47.

D. R. Ney "Volumetric Rendering of Computed Tomography Data: Principles and Techniques;" *IEEE Computer Graphics and Applications*, 1990; 24-32.

N. M. Alpert et al., "The Principal Axes Transformation—A Method for Image Registration;" *The Journal of Nuclear Medicine*; 1990; 31:1717-1722.

P.A. van den Elsen et al.; "Medical Image Matching—A Review with Classification;" *IEEE Engineering in Medicine and Biology*, 1993; 26-38.

G. T. Barnes et al.; "Conventional and Spiral Computed Tomography: Physical Principles and Image Quality Considerations;" *Computed Body Tomography*, 1998, Lippincot-Raven, Philadelphia, PA pp. 1-20.

Milan Sonka and J. Michael Fitzpatrick (eds); *Handbook of Medical Imaging* vol. 2. *Medical Image Processing and Analysis*; pp. 129-174 & 447-506.

W. M. Feinberg et al.; "Prevalence, Age Distribution, and Gender of Patients with Atrial Fibrillation;" *Arch. Intern. Med.* vol. 155; Mar. 1995; pp. 469-473.

J. L. Cox, J. P. Boineau, R. B. Schuessler, T. B. Ferguson, Jr., M. E. Cain, B. D. Lindsay, P. B. Corr, K. M. Kater, D. G. Lappas; "Operations for Atrial Fibrillation;" Electrophysiology, Pacing and Arrhythmia, Clin. Cardiol. 14, 1991; pp. 827-834.

M. Haissaguerre, P. Jais, S. C. Shah, A. Takahashi, M. Hocini, G. Quiniou, S. Garrigue, A. Le Mouroux, P. Le Metayer, and J. Clementy; "Spontaneous Initiation of Atrial Fibrillation by Ectopic Beats Originating in the Pulmonary Viens;" The New England Journal of Medicine, vol. 339, No. 10, Sep. 3, 1998; pp. 659-668.

C. Pappone, S. Rosanio, G. Augello, G. Gallus, G. Vicedomini, P. Mazzone, S. Gulletta, F. Gugliotta, A. Pappone, V. Santinelli, V. Tortoriello, S. Sala, A. Zangrillo, G. Crescenzi, S. Benussi, and O. Alfieri; "Mortality, Morbidity, and Quality of Life After Circumferential Pulmonary Vein Ablation for Atrial Fibrillation;" Journal of the American College of Cardiology, vol. 42, No. 2; 2003; 185-197.

J. Sra et al., "Current Problems in Cardiology- Atrial Fibrilliation: Epidemiology, Mechanisms, and Management:" Current Problems in Cardiology, Jul. 2000; pp. 406-524.

ACC/AHA/ESC Practise Guidelines; Eur. Heart J., vol. 22, issue 20, Oct. 2001; pp. 1854-1923.

M. D. Leash, T. Trepelse, H. Omran, A. Bartorelli, P. Della Bella, T. Nakai, M. Reisman, D. fleschenberb, U. Krumsdorf, and D. Scherer; "Tiny Device Blocks 'Usless' Part of Heart, prevents blood clots;" Journal Report; American Heart Association; Apr. 9, 2002.

Ellen Barlow; "Operating in 3-D" found at www.med.harvard.edu/publications/HMAB/196fo3d.html.

W. M. feinberg, J. L. Blackshear, A. Laupacis, R. Kronmal, and R. G. Hart; "Prevalence, Age Distribution, and Gender of Patients with Atrial Fibrillation;" Arch Intern Med., vol. 155, Mar. 13, 1995; pp. 469-473.

C. Pappone, S. Rosanio, G. Augello, G. Gallus, G. Vicedomini, P. Mazzone, S. Gulletta, F. Gugliotta, A. Pappone, V. Santinelli, V. Tortoriello, S. Sala, A. Zangrillo, G. Crescenzi, S. Benussi, and O. Alfieri; "Mortality, Morbidity, and Quality of Life After Circumferential Pulmonary Vein Ablation for Atrial Fibrillation;" Journal of the American College of Cardiology, vol. 42, No. 2; 2003; 185-197.

"Current Problems in Cardiology- Atrial Fibrilliation: Epidemiology, Mechanisms, and Management;" Current Problems in Cardiology, Jul. 2000; pp. 406-524.

"Tiny Device Blocks Unless Part of Heart, Prevents Blood Clots," Apr. 9, 2002; found at www.americanheart.org/presenter.jhtml?identifier=3001890.

"Operating in 3-D," Harvard Medical Alumni Bulletin, Ellen Barlow, found at www.med.harvard.edu/publications/HMAB/196fo3d.html.

"Advanced Vessel Analysis" product descritpoin, [online] http://www.gehealthcare.com/usen/ct/clin_app/products/aswessel.html [retrieved Dec. 1, 2004].

"CardilQ" product description, [online], http://egems.gehealthcare.com/geCommunity/Europe/flex_trial/awFlexTrial/aw3_1/eflextrial [retrieved Dec. 1, 2004].

Genevieve Derumeaux et al., Doppler Tissue Imaging Quantitates Regional Wall Motion During Myocardial Ischemia and Reperfusion, Circulation Journal of the American Heart Association, Circulation 1998; 97; 1970-1977.

Olivier Gerard et al., Efficient Model-Based Quantification of Left Ventricular Function in 3-D Echocardiography. IEEE Transactions on Medical Imaging, 21 (9): pp. 1059-1068, Sep. 2002.

Wahle et al., 3D Heart Vessel Reconstruction from Biplane Angiograms, IEEE Computer Graphics and Applications, 16(1): pp. 65-73, Jan. 1996.

Helmut Mair et al., Epicardial Lead Implantation Techniques for Biventricular Pacing via Left Lateral Mini-Thoracotomy, Video Assisted Thoracoscopy and Robotic Approach, The Heart Surgery Forum, 6(5): pp. 412-417, Mar. 2003.

Toshiko Nakai, Michael D. Lesh, Edward P. Gerstenfeld, Renu Virmani, Russell Jones and Randall J. Lee; "Percutaneous Left Atrial Appendage Occlusion (PLAATO) for Preventing Cardioembolism: First Experience in Canine Model", Circulation 2002; 105;2217-2222; originally published online Apr. 15, 2002; American Heart Association; http://circ.ahajounals.org/cgi/content/full/105/18/2217.

Sra et al., "Registration of Three-Dimensional Left Atrial Computed Tomographic Images With Projection Images Obtained Using Fluoroscopy", Circulation 2005; 112: 3763-3768.

\* cited by examiner

CARDIAC CT SYSTEM AND METHOD FOR PLANNING AND TREATMENT OF BIVENTRICULAR PACING USING EPICARDIAL LEAD

BACKGROUND OF THE INVENTION

The present disclosure relates generally to cardiac rhythm management systems and, more particularly, to a cardiac imaging system and method for planning biventricular pacing using an epicardial lead.

It is estimated that approximately 6-7 million people in the United States and Europe alone have congestive heart failure (CHF), with ischemic and idiopathic cardiomyopathies being the most common causes of CHF. In about 20-50% of patients having CHF, the associated electrocardiograms are characterized by prolonged PR intervals and wide QRS complexes. Moreover, about 29% of these patients have left bundle branch block (LBBB).

In a normal heartbeat, the electrical conduction begins in the sinoatrial (SA) node (a small group of muscle cells in the upper right part of the upper right heart chamber, i.e., the right atrium). Impulses sent out by the SA node spread quickly throughout the upper heart chamber and across the atrioventricular (AV) node. Once past the AV node, the electrical signals travel through a bunch of fibers called the bundle of His, which passes the signals the rest of the way through the wall separating the upper and lower heart chambers, splitting down the right and left bundle branches to reach each part of the ventricles.

However, in those patients with CHF and LBBB, a long mechanical delay in the left side of the heart leads to a delayed left ventricular ejection due to delayed left ventricular depolarization. In other words, LBBB causes an asymmetrical contraction of the right and left ventricles. In addition, this condition may also result in different regions of the left ventricle not contracting in a coordinated fashion. This irregular motion is characterized by shortening of the septum, followed by stretching of the lateral wall. Subsequently, the lateral wall then shortens and the septum stretches, thereby causing an ineffective contraction of the left ventricle.

Cardiac resynchronization therapy, also known as biventricular pacing, is an interventional procedure in which both the right ventricle and left ventricle of the heart are paced simultaneously to improve heart pumping efficiency. In one example of a conventional biventricular pacing procedure, both the right ventricle and right atrial leads are first positioned. Then, a sheath is positioned within the coronary sinus (CS) and a CS angiogram is performed in order to delineate a suitable branch for left ventricle lead placement. After a suitable branch is identified, the left ventricle lead is placed in the posterior or posterolateral branch of the CS. Once positioned, the right and left ventricle leads are paced simultaneously, thus achieving synchronization with atrial contraction.

For many patients, cannulating the CS is the one-step procedure of choice for biventricular lead placement. However, in over 20% of these patients, lead placement in the CS may be an unsuccessful or very lengthy procedure, or the lead may become dislodged from the CS. Other difficulties with this lead placement procedure may also include unavailability of a suitable CS branch, significant rotation of the CS due to left atrium and left ventricle dilation, and the presence of the Tebesian valve therein. In most instances, these problems are identified only at the time of the interventional procedure, and thus the procedure is typically either completely abandoned or the patient is brought back into the operating room for a second procedure where, through the use of a surgical incision, an expensive and invasive procedure, the left ventricle lead is placed epicardially.

Unfortunately, epicardial lead placement is not without its own pitfalls, some of which include: a limited view of the posterolateral area of the left ventricle using minithoracotomy; the limitation of placement sites providing reasonable pacing and sensing parameters; the inability to determine the distance of the left ventricle from the thoracic wall; the inability to identify the posterolateral area of the left ventricle that contracts last; the potential risk of damaging the coronary arteries and veins; the increased level of difficulty due to the presence of extrapericardial fat; the lack of visualization of normal versus scarred tissue; and the difficulty in identifying the ideal pacing position as a result of one or more of the above.

Accordingly, there is a need for an improved system and method for determining an effective roadmap for CS anatomy and, where appropriate, a roadmap for effective epicardial lead placement.

BRIEF DESCRIPTION OF THE INVENTION

The above discussed and other drawbacks and deficiencies of the prior art are overcome or alleviated by a method for planning biventricular pacing lead placement for a patient. In an exemplary embodiment, the method includes obtaining non-invasive acquisition data from a medical imaging system and generating a 3D model of the left ventricle and thoracic wall of the patient from these data. One or more left ventricle anatomical landmarks are identified on the 3D model, and saved views of the 3D model are registered on an interventional system. One or more of the registered saved views are visualized with the interventional system, and at least one suitable region on the left ventricle wall is identified for epicardial lead placement.

In another aspect, a method for planning biventricular pacing lead placement for a patient includes obtaining acquisition data from a medical imaging system using a protocol optimized for imaging the thoracic wall and left ventricle. The acquisition data are segmented using a 3D protocol and short axis protocols so as to visualize the thoracic wall, LV walls, coronary arteries and veins in the adjacent regions and epicardial fat. A 3D model of the left ventricle and thoracic wall of the patient is generated and one or more left ventricle anatomical landmarks on the 3D model are identified. Saved views of the 3D model are registered on an interventional system, and one or more of the registered saved views are visualized with the interventional system. At least one suitable region on the left ventricle wall is identified for epicardial lead placement.

In still another aspect, a method for planning biventricular pacing lead placement for a patient includes obtaining acquisition data from a cardiac computed tomography (CT) imaging system using a protocol directed toward the thoracic wall and left ventricle. The acquisition data are segmented using a 3D protocol and short axis protocols so as to visualize the thoracic wall, LV walls, coronary arteries and veins, and epicardial fat. A 3D model of the left ventricle and thoracic wall of the patient is generated, and a movement profile of the posterolateral wall relative to the external chest wall is obtained. In addition, one or more left ventricle anatomical landmarks are identified on the 3D model, and saved views of the 3D model are registered on a fluoroscopy system. One or more of the registered saved views are visualized with the fluoroscopy system, and at least one suitable region on the left ventricle wall is identified for epicardial lead placement.

In still another aspect, a system for planning biventricular pacing lead placement for a patient includes a medical imaging system for generating acquisition data and an image generation subsystem for receiving the acquisition data and for generating one or more images of the left ventricle and thoracic wall of the patient. An operator console is used for identifying one or more left ventricle anatomical landmarks on one or more of the images, and a workstation includes post-processing software for registering saved views of the 3D model on an interventional system. The interventional system is configured for visualizing one or more of the registered saved views therewith and for identifying at least one suitable region on the left ventricle wall for epicardial lead placement.

In still another aspect, a system for planning biventricular pacing lead placement for a patient includes a cardiac computed tomography (CT) imaging system for generating acquisition data, the CT imaging system using a protocol directed toward the thoracic wall and left ventricle, and a fluoroscopic imaging system used during intervention. An image generation subsystem receives the acquisition data and generates one or more images of the left ventricle and thoracic wall of the patient. The image generation system is further configured for segmenting the acquisition data using a 3D protocol and short axis protocols so as to visualize the thoracic wall, LV walls, coronary arteries and veins, and epicardial fat. An operator console is used for identifying one or more left ventricle anatomical landmarks on one or more images, and a workstation includes post-processing software for registering saved views of the 3D model on a fluoroscopy system. The fluoroscopy system is configured for visualizing one or more of the registered saved views therewith and for identifying at least one suitable region on the left ventricle wall for epicardial lead placement.

BRIEF DESCRIPTION OF THE DRAWINGS

Referring to the exemplary drawings wherein like elements are numbered alike in the several Figures.

DETAILED DESCRIPTION OF THE INVENTION

Disclosed herein is a cardiac computed tomography (CT) system and method for biventricular pacing that provides information for planning interventional procedures that enable an electrophysiologist, cardiologist and/or surgeon to plan in advance a desired approach to complete the procedure. Additionally, with a more detailed three-dimensional (3D) geometrical representation of the left ventricle (LV) and its relationship to the thoracic wall, the practitioner can also identify the presence of fat, the location and orientation of the major blood vessels and their branches, and viable tissue. This information can be used for determining the optimal placement of the LV lead. Additionally, LV contractility and regional wall motion abnormalities can be visualized to identify the best location for placement of LV epicardial pacing lead. Thus, the information obtained from cardiac CT system eliminates the need to place the lead blindly, thereby avoiding many of the problems discussed above. Moreover, the obtained information allows for direct epicardial lead placement via a surgical incision or endoscopic approach at the most beneficial location, as the location of the incision and the lead placement may be planned in advance. Furthermore, the epicardial lead could also be registered with an interventional system or fluoroscopy so as to enable precise placement of the lead.

Although the exemplary embodiments illustrated hereinafter are described in the context of a CT imaging system, it will be appreciated that other imaging systems known in the art are also contemplated with regard to planning biventricular epicardial lead placement.

Figure 1:
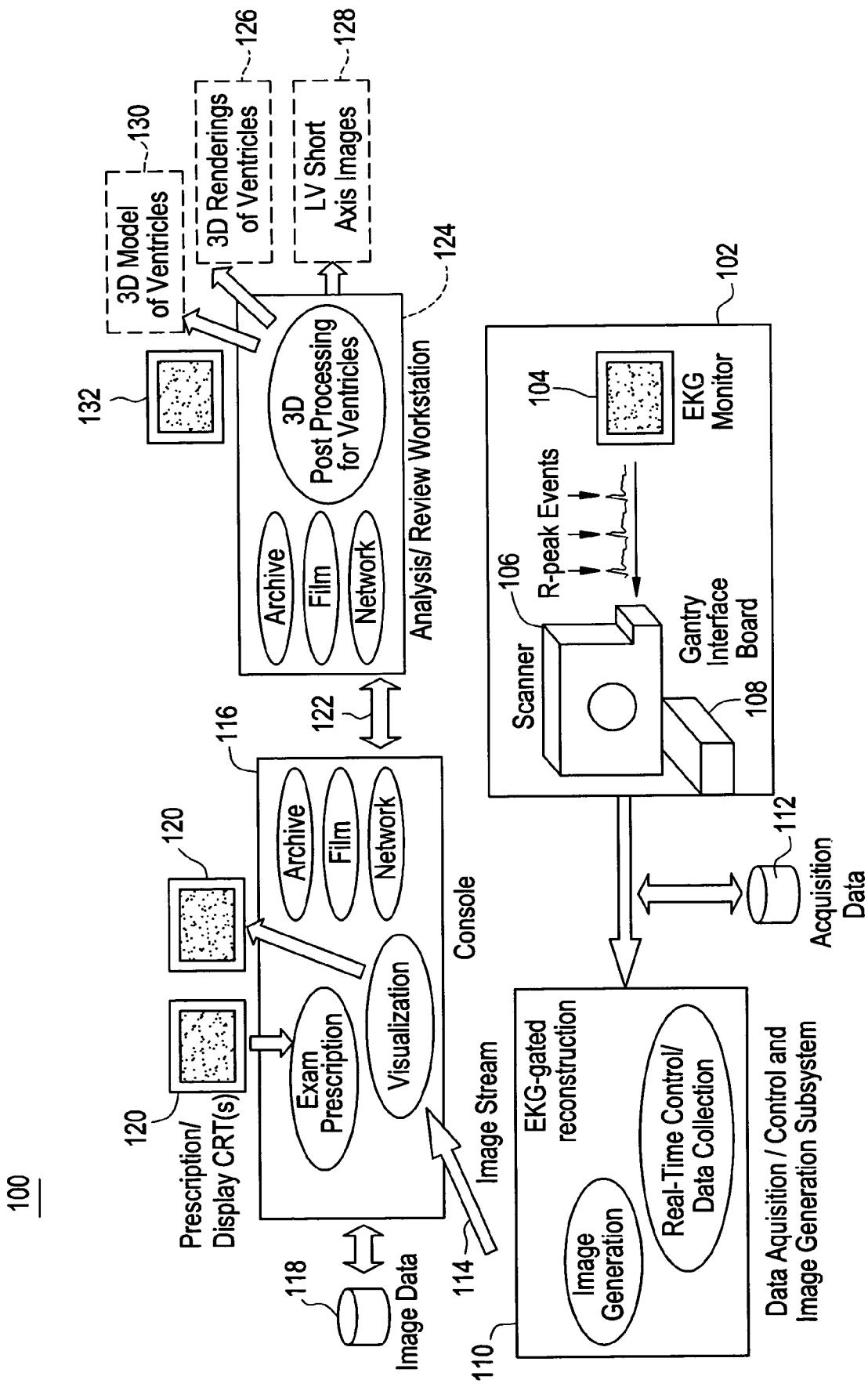
FIG. 1 is a schematic diagram of a medical imaging system, such as a computed tomography (CT) system, suitable for planning biventricular lead pacing, in accordance with an embodiment of the invention.

Referring initially to FIG. 1, there is shown an overview of an exemplary cardiac computed tomography (CT) system 100 with support for cardiac imaging. Again, it should be understood that the cardiac CT system 100 is presented by way of example only, since other imaging systems known in the art (e.g., magnetic resonance, ultrasound) may also be used in an embodiment of the present invention. A scanner portion 102 of the system 100 includes an EKG monitor 104 that outputs R-peak events into a scanner 106 through a scanner interface board 108. A suitable example of scanner interface board 108 is a Gantry interface board, and can be used to couple an EKG system to the scanner. The cardiac CT subsystem defined by scanner portion 102 utilizes EKG-gated acquisition or image reconstruction capabilities to image the heart free of motion in its diastolic phase, as well as in multiple phases of systole and early diastole.

Data are outputted from the scanner portion 102 into a subsystem 110 that includes software for performing data acquisition, data control and image generation. In addition, data that is outputted from the scanner 106, including R-peak time stamps, is stored in an acquisition database 112. Acquisition is performed according to one or more acquisition protocols that are optimized for imaging the heart and specifically the LV diastole and multiple phases in systole and early diastole. Image generation is performed using one or more optimized 3D protocols for automated image segmentation of the CT image dataset for the LV and thoracic wall.

The image data stream 114 is sent to an operator console 116. The data used by software at the operator console 116 for exam prescription and visualization is stored in an image database 118, along with the data from the image data stream 114. Display screens 120 are provided to the operator of the exam prescription and visualization processes. The image data may be archived, put on film or sent over a network 122 to a workstation 124 for analysis and review, including 3D post processing. The post processing software depicted in the workstation 124 includes one or more optimized 3D protocols and short axis protocols from an automated image segmentation of the CT image dataset for the LV anatomy, movement of LV walls during systole (i.e., LV contractility), epicardial fat location, location of viable tissue, blood vessels and their branches and orientation.

The 3D protocols and short axis protocols of the post processing software enable the software to provide views of the LV, including blood vessels, branches and slow motion cine of the LV, particularly the posterolateral wall of the LV. These special views and video (cine) clips may be saved into a 3D rendering of ventricle files 126 and LV short axis images 128 for use by the practitioner for interventional planning and procedure. The post processing software also provides for the export of detailed 3D models 130 of the thoracic wall and ventricle surfaces. The 3D models 130 (which may be viewed on display screen 132 associated with workstation 124) are configured to include geometric markers inserted into the volume at landmarks of interest such that the thoracic wall and the LV are visualized in a translucent fashion with the opaque geometric landmarks.

In addition, the 3D models 130 may be in exported in any of several formats, including but not limited to: a wire mesh geometric model, a set of contours, a segmented volume of binary images, and a DICOM (Digital Imaging and Communications in Medicine) object using the radiation therapy (RT) DICOM object standard or similar object. Other formats known in the art can also be used to store and export the 3D models 130.

Figure 2:
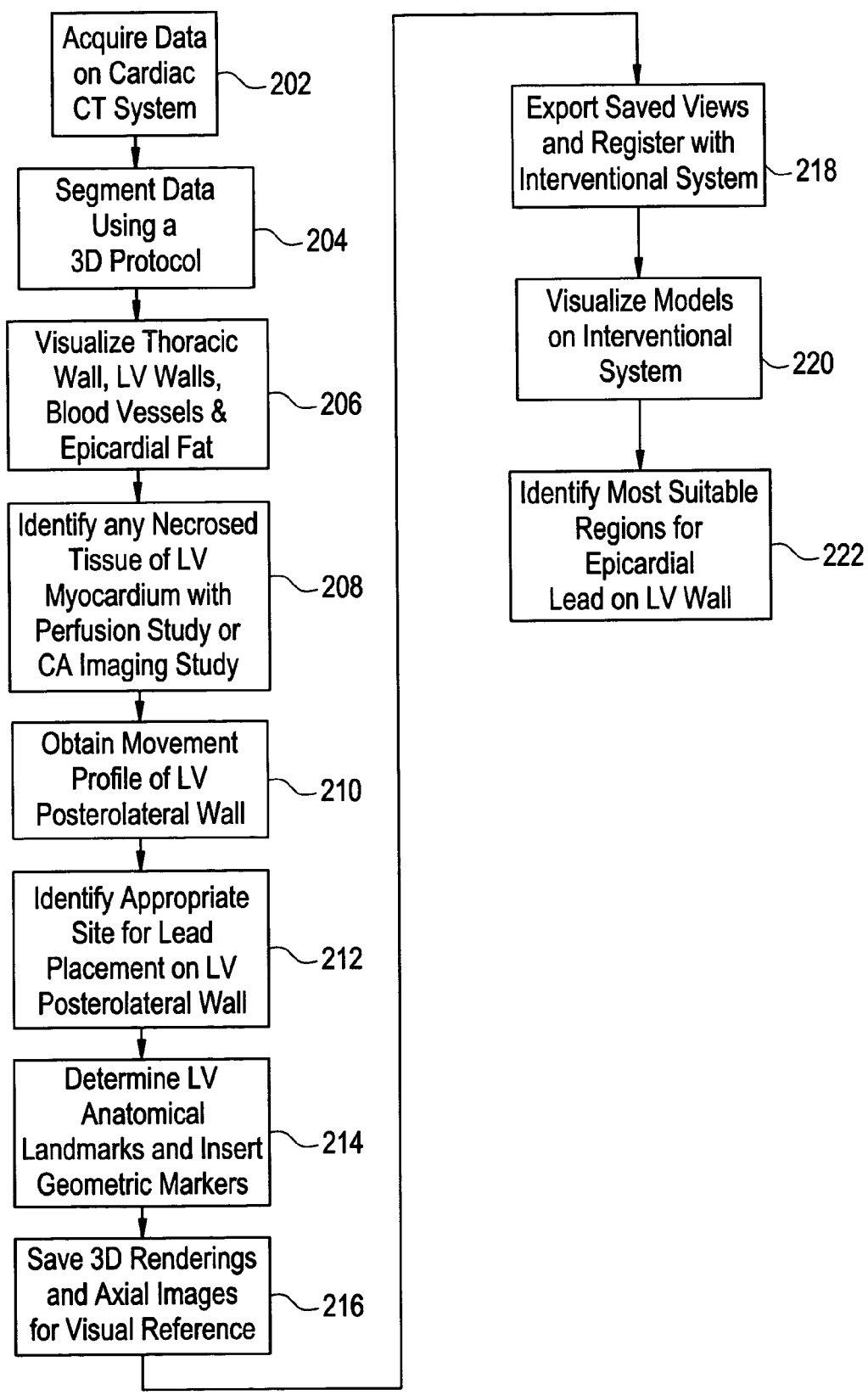
FIG. 2 is a flow diagram of a method for planning biventricular pacing epicardial lead placement, in accordance with a further embodiment of the invention.

Referring now to FIG. 2, there is shown a flow diagram 200 illustrating a method for interventional planning of bi-ventricular pacing lead placement, in accordance with a further embodiment of the invention. Beginning at block 202, a volume of data is initially acquired on the cardiac CT system, using a protocol that is preferably optimized for the thoracic wall and LV regions of the heart. At block 204, the image dataset is segmented with post-processing software using a 3D protocol and short axis protocols designed to extract the surface of the LV and the LV myocardium. Automated procedures may be employed, where appropriate, with or without queues from the operator (e.g., location of anteroposterior, left anterior oblique, posterolateral, oblique and right anterior oblique views).

Then, as shown in block 206, the thoracic wall, LV walls, blood vessels and epicardial fat are visualized using 3D surface and/or volume rendering. The perfusion and/or viability of the posterolateral myocardium of the LV may also be visualized with a perfusion study or with images of the coronary artery imaging study so as to identify any necrosed tissue of the LV myocardium, if existing. This is illustrated at block 208. As shown in block 210, the movement profile (i.e., contractility) of the LV posterolateral wall close to the external chest well is obtained from the LV functional images. In particular, the contraction pattern of the posterolateral wall of LV is determined in order to identify most appropriate site for lead placement, as shown at block 212.

The method 200 then proceeds to block 214, wherein explicit geometric markers are inserted into the volume at landmarks of interest, and wherein the thoracic wall and LV can be visualized in a translucent fashion with the inserted opaque geometric landmarks. As illustrated at block 216, specific 3D renderings and axial images (as DICOM images, video clips, films, multimedia formats, etc.) are saved as desired for subsequent visual reference during the interventional planning. The saved views are then exported and registered with the projection image on the fluoroscopy system or alternatively, with the tomosynthesis images of the 3D fluoroscopy system, as shown in block 218.

Finally, the interventional system is accessed and the imported, registered models therewith are visualize d by the practitioner, as shown in block 220. Then, at block 222, the practitioner then identifies the most suitable area for placement of the epicardial pacing electrode on the LV wall, as well as the next best region(s) for placement thereof. In particular, the practitioner may identify the blood vessels on the epicardium of the left ventricle and eliminate the blood vessels and/or the myocardium directly under the blood vessels as a suitable region.

It will be appreciated that automatic techniques may be employed to perform any of the above steps by using one or more of the several computer-assisted detection, localization and visualization methods available, such as quantitative analysis of perfusion defects, localized contractility profile (LV wall movement), identification of blood vessels using the continuity of same intensity levels. Moreover, these methods could be either completely automatic when the procedure and the organ of interest is specified or partly interactive with input from the user.

It will further be appreciated that through the use of the above described method and system embodiments, the planning of bi-ventricular pacing is improved in that the imaging information generated and registered allows for an appropriately tailored approach to the interventional procedure. In choosing the appropriate approach, the duration of the procedure itself is reduced and any unnecessary procedures are also eliminated. More particularly, a detailed 3D geometric and axial representation of the LV and thoracic wall increases the precision of the biventricular pacing procedure. The identification of necrosed myocardium, if any, enables the electrophysiologist/cardiac surgeon to avoid such areas and place the LV epicardial lead on healthy, viable myocardium.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method for planning biventricular pacing lead placement for a patient, the method comprising:
   obtaining acquisition data from a medical imaging system;
   generating a 3D model of the left ventricle and thoracic wall of the patient from the acquisition data, prior to performing a biventricular pacing procedure on the patient;
   identifying one or more left ventricle anatomical landmarks on said 3D model and inserting geometric markers therein corresponding to selected ones of said anatomical landmarks;
   registering saved views of said 3D model on an interventional system; and
   visualizing one or more of said registered saved views with said interventional system; and
   identifying, prior to utilizing said interventional system, at least one suitable region on the left ventricle wall for epicardial lead placement so as to facilitate the biventricular lead placement.

2. The method of claim 1, further comprising determining, from said 3D model, any necrosed tissue of the LV myocardium, wherein the identification of any sites of such necrosed tissue is used to eliminate said sites of such necrosed tissue from epicardial lead placement.

3. The method of claim 1, wherein said obtaining acquisition data is implemented with protocols directed for imaging the LV and thoracic wall.

4. The method of claim 1, wherein said identifying at least one suitable region further includes identifying the blood vessels on the epicardium of the left ventricle and eliminating at least one of the blood vessels and the myocardium directly under the blood vessels as a suitable region.

5. The method of claim 3, further comprising utilizing post processing software to process said acquisition data so as to generate short axis images of the LV and thoracic wall.

6. The method of claim 5, wherein said 3D model and said short axis images are visualized through a display screen associated with said interventional system.

7. The method of claim 1, further comprising obtaining a movement profile of the LV posterolateral wall.

8. The method of claim 1, wherein said obtaining acquisition data is EKG gated.

9. A method for planning biventricular pacing lead placement for a patient, the method comprising:
   obtaining acquisition data from a medical imaging system using a protocol directed toward the thoracic wall and left ventricle;
   segmenting said acquisition data using a 3D protocol and short axis protocols so as to visualize the thoracic wall, LV walls and epicardial fat;
   generating a 3D model of the left ventricle and thoracic wall of the patient from the acquisition data, prior to performing a biventricular pacing procedure on the patient;
   identifying one or more left ventricle anatomical landmarks on said 3D model and inserting geometric markers therein corresponding to selected ones of said anatomical landmarks;
   registering saved views of said 3D model on an interventional system; and
   visualizing one or more of said registered saved views with said interventional system; and
   identifying, prior to utilizing said interventional system, at least one suitable region on the left ventricle wall for epicardial lead placement so as to facilitate the biventricular lead placement.

10. The method of claim 9, further comprising determining, from said 3D model, any necrosed tissue of the LV myocardium, wherein the identification of any sites of such necrosed tissue is used to eliminate said sites of such necrosed tissue from epicardial lead placement.

11. The method of claim 9, wherein said obtaining acquisition data is implemented with protocols directed for imaging the LV and thoracic wall.

12. The method of claim 9, wherein said identifying at least one suitable region further includes identifying the blood vessels on the epicardium of the left ventricle and eliminating at least one of the blood vessels and the myocardium directly under the blood vessels as a suitable region.

13. The method of claim 11, further comprising utilizing post processing software to process said acquisition data so as to generate short axis images of the LV and thoracic wall.

14. The method of claim 13, wherein said 3D model and said short axis images are visualized through a display screen associated with said interventional system.

15. The method of claim 9, further comprising obtaining a movement profile of the LV posterolateral wall.

16. The method of claim 9, wherein said obtaining acquisition data is EKG gated.

17. The method of claim 9, wherein said medical imaging system is one of a computed tomography system, a magnetic resonance imaging system and an ultrasound system.

18. A method for planning biventricular pacing lead placement for a patient, the method comprising:
   obtaining acquisition data from a cardiac computed tomography (CT) imaging system using a protocol directed toward the thoracic wall and left ventricle;
   segmenting said acquisition data using a 3D protocol and short axis protocols so as to visualize the thoracic wall, LV walls and epicardial fat;
   generating a 3D model of the left ventricle and thoracic wall of the patient from the acquisition data, prior to performing a biventricular pacing procedure on the patient;
   obtaining a movement profile of the posterolateral wall relative to the external chest wall;
   identifying one or more left ventricle anatomical landmarks on said 3D model and inserting geometric markers therein corresponding to selected ones of said anatomical landmarks;
   registering saved views of said 3D model on a fluoroscopy system; and
   visualizing one or more of said registered saved views with said fluoroscopy system; and
   identifying, prior to utilizing said interventional system, at least one suitable region on the left ventricle wall for epicardial lead placement so as to facilitate the biventricular lead placement.

19. The method of claim 18, further comprising determining, from said 3D model, any necrosed tissue of the LV myocardium, wherein the identification of any sites of such necrosed tissue is used to eliminate said sites of such necrosed tissue from epicardial lead placement.

20. The method of claim 18, wherein said obtaining acquisition data is implemented with protocols optimized for imaging the LV and thoracic wall.

21. The method of claim 18, wherein said identifying at least one suitable region further includes identifying the blood vessels on the epicardium of the left ventricle and eliminating at least one of the blood vessels and the myocardium directly under the blood vessels as a suitable region.

22. The method of claim 20, further comprising utilizing post processing software to process said acquisition data so as to generate short axis images of the LV and thoracic wall.

23. The method of claim 22, wherein said 3D model and said short axis images are visualized through a display screen associated with said fluoroscopy system.

24. The method of claim 19, wherein said obtaining acquisition data is EKG gated.

25. A system for planning biventricular pacing lead placement for a patient, comprising:
   a medical imaging system for generating acquisition data;
   an image generation subsystem for receiving said acquisition data and generating one or more 3D model images of the left ventricle and thoracic wall of the patient from the acquisition data, prior to performance of a biventricular pacing procedure on the patient;
   an operator console for identifying one or more left ventricle anatomical landmarks on said one or more images and inserting geometric markers therein corresponding to selected ones of said anatomical landmarks;
   a workstation including post processing software for registering saved views of said 3D model on an interventional system; and
   wherein said interventional system is configured for visualizing one or more of said registered saved views therewith and identifying, prior to utilizing said interventional system, at least one suitable region on the left ventricle wall for epicardial lead placement so as to facilitate the biventricular lead placement.

26. The system of claim 25, wherein said workstation is configured for determining, from said 3D model, any necrosed tissue of the LV myocardium.

27. The system of claim 25, wherein said image generation subsystem is configured with protocols directed for imaging the LV and thoracic wall.

28. The system of claim 25, wherein said identifying at least one suitable region further includes identifying the blood vessels on the epicardium of the left ventricle and eliminating at least one of the blood vessels and the myocardium directly under the blood vessels as a suitable region.

29. The system of claim 27, wherein said post processing software is further configured to process said acquisition data so as to generate short axis images of the LV and thoracic wall.

30. The system of claim 29, further comprising a display screen associated with said interventional system, said display screen for visualizing said 3D model and said short axis images.

31. The system of claim 26, wherein said image generating subsystem is EKG gated.

32. A system for planning biventricular pacing lead placement for a patient, comprising:
- a cardiac computed tomography (CT) imaging system for generating acquisition data, said CT imaging system using a protocol directed toward the thoracic wall and left ventricle;
- an image generation subsystem for receiving said acquisition data and generating one or more 3D model images of the left ventricle and thoracic wall of the patient from the acquisition data, prior to performance of a biventricular pacing procedure on the patient;
- said image generation subsystem further configured for segmenting said acquisition data using a 3D protocol and short axis protocols so as to visualize the thoracic wall, LV walls and epicardial fat;
- an operator console for identifying one or more left ventricle anatomical landmarks on said one or more images and inserting geometric markers therein corresponding to selected ones of said anatomical landmarks;
- a workstation including post processing software for registering saved views of said 3D model on a fluoroscopy system; and
- wherein said fluoroscopy system is configured for visualizing one or more of said registered saved views therewith and identifying, prior to utilizing said interventional system, at least one suitable region on the left ventricle wall for epicardial lead placement so as to facilitate the biventricular lead placement.

33. The system of claim 32, wherein said workstation is configured for determining, from said 3D model, any necrosed tissue of the LV myocardium.

34. The system of claim 32, wherein said post processing software is further configured to process said acquisition data so as to generate short axis images of the LV and thoracic wall.

35. The system of claim 32, wherein said identifying at least one suitable region further includes identifying the blood vessels on the epicardium of the left ventricle and eliminating at least one of the blood vessels and the myocardium directly under the blood vessels as a suitable region.

36. The system of claim 34, further comprising a display screen associated with said fluoroscopy system, said display screen for visualizing said 3D model and said short axis images.

37. The system of claim 32, wherein said image generating subsystem is EKG gated.

* * * * *